(12) United States Patent
Friedrich (10) Patent No.: US 10,562,719 B2
(45) Date of Patent: Feb. 18, 2020

(54) PNEUMATIC-TUBE CONTAINER

(71) Applicant: ING. SUMETZBERGER GMBH, Vienna (AT)

(72) Inventor: Peter Friedrich, Vienna (AT)

(73) Assignee: ING. SUMETZBERGER GMBH, Vienna (AT)

( * ) Notice: Subject to any disclaimer, the term of this patent is extended or adjusted under 35 U.S.C. 154(b) by 0 days.

(21) Appl. No.: 16/346,495

(22) PCT Filed: Nov. 6, 2017

(86) PCT No.: PCT/AT2017/060294
§ 371 (c)(1),
(2) Date: Apr. 30, 2019

(87) PCT Pub. No.: WO2018/085871
PCT Pub. Date: May 17, 2018

(65) Prior Publication Data
US 2019/0291973 A1 Sep. 26, 2019

(30) Foreign Application Priority Data
Nov. 8, 2016 (AT) .............................. A 51018/2016

(51) Int. Cl.
*B65G 51/06* (2006.01)
*G01N 35/04* (2006.01)

(52) U.S. Cl.
CPC .............. *B65G 51/06* (2013.01); *G01N 35/04* (2013.01); *G01N 2035/0405* (2013.01); *G01N 2035/0481* (2013.01)

(58) Field of Classification Search
CPC ........... B65G 51/06; G01N 2035/0481; G01N 2035/0405
(Continued)

(56) References Cited

U.S. PATENT DOCUMENTS 3,072,362 A * 1/1963 Allen ..................... B65G 51/06
406/188
3,733,037 A * 5/1973 Vandiveer .............. B65G 51/06
406/189
(Continued)

FOREIGN PATENT DOCUMENTS

AT 12017 U1 9/2011
EP 0697354 A 2/1996
(Continued)

*Primary Examiner* — Joseph A Dillon, Jr.
(74) *Attorney, Agent, or Firm* — Lucas & Mercanti, LLP; Klaus P. Stoffel (57) ABSTRACT

A pneumatic-tube container having a container cylinder and having a cover and a base, at least the cover can be moved from a closed position into an open position. The container cylinder contains an insert, which has at least one tubular channel extending parallel to the longitudinal axis of the container cylinder. At least one channel contains at least one clamping element, which projects laterally into the channel. The damping element can be moved out of the channel, wherein the movement out of the channel and into the same is coupled to the movement of the cover from the closed position into the open position and from the open position into the closed position, respectively. When the cover is open, and preferably also when the base is open, the sample tubes therefore fall out due to gravity when the pneumatic-tube container is held with the opening in the downward direction.

4 Claims, 7 Drawing Sheets

(58) Field of Classification Search
USPC .................................................. 406/187, 188
See application file for complete search history.

(56) References Cited

U.S. PATENT DOCUMENTS

| | | | | |
|---|---|---|---|---|
| 4,032,066 A * | 6/1977 | Wright | ................... | B04B 5/0421 |
| | | | | 494/20 |
| 4,362,443 A * | 12/1982 | Mallory | ................. | B65G 51/06 |
| | | | | 406/188 |
| 4,876,068 A * | 10/1989 | Castaneda | ............. | B01L 3/5082 |
| | | | | 422/401 |
| 5,092,714 A * | 3/1992 | Porter | .................... | B65G 51/06 |
| | | | | 406/111 |
| 5,727,455 A * | 3/1998 | Yerman | ................... | A61L 11/00 |
| | | | | 100/215 |
| 6,015,246 A * | 1/2000 | Yamane | ................. | B65G 51/06 |
| | | | | 406/184 |
| 6,062,398 A * | 5/2000 | Thalmayr | ................ | B01L 9/06 |
| | | | | 206/443 |
| 6,477,442 B1 * | 11/2002 | Valerino, Sr. | .......... | B65G 51/34 |
| | | | | 414/730 |
| 7,275,647 B1 * | 10/2007 | Thompson | ............ | A47B 81/007 |
| | | | | 211/85.18 |
| 8,304,186 B2 * | 11/2012 | Stibelli | ................... | B01L 3/502 |
| | | | | 435/283.1 |
| 8,439,216 B1 * | 5/2013 | Walck | ...................... | B01L 3/508 |
| | | | | 141/65 |
| 2006/0120834 A1 * | 6/2006 | Pressman | ............... | B01D 61/18 |
| | | | | 414/331.01 |
| 2014/0319163 A1 * | 10/2014 | Lukhaub | ................. | G01N 35/04 |
| | | | | 221/1 |
| 2018/0224476 A1 * | 8/2018 | Birrer | .................... | B65G 54/02 |

FOREIGN PATENT DOCUMENTS

| | | |
|---|---|---|
| EP | 0706961 A1 | 4/1996 |
| EP | 0761576 A2 | 3/1997 |
| EP | 2657160 A1 | 10/2013 |
| WO | 2013056281 A1 | 4/2013 |

* cited by examiner

PNEUMATIC-TUBE CONTAINER

CROSS-REFERENCE TO RELATED APPLICATIONS

The present application is a 371 of International application PCT/AT2017/060294, filed Nov. 6, 2017, which claims priority of AT A51018/2016, filed Nov. 8, 2016, the priority of these applications is hereby claimed and these applications are incorporated herein by reference.

TECHNICAL FIELD

The present invention relates to a pneumatic-tube container having a container cylinder and having a cover and a base at the two ends of the container cylinder, wherein at least the cover is movable from a closed position to an open position, wherein the container cylinder accommodates an insert which, in order to receive sample tubes, has at least one tubular channel extending parallel to the longitudinal axis of the container cylinder, wherein at least one channel accommodates at least one clamping element, which protrudes laterally into the channel.

PRIOR ART

Pneumatic-tube containers are often used in hospitals to transport blood samples that are located in sample tubes. The transport of such sample tubes must satisfy special requirements. Firstly, such sample tubes may break if two sample tubes strike each other, since the forces that arise during the transport of pneumatic-tube containers are considerable. Secondly, even if the sample tubes do not break, strong vibrations lead to hemolysis in the blood, which renders the blood sample unusable. (In hemolysis, the red blood cells break open, such that their contents mix with the blood plasma and thus falsify the blood plasma values).

Therefore, various proposals have already been made as regards how to fix the sample tubes in the pneumatic-tube container such that they cannot strike against the wall of the pneumatic-tube container or against each other. A solution of this kind is described in patcit0001: AT 12017—.

U1. There, an insert is used having a framework which is coaxial to the pneumatic-tube container and which consists of a support column with at least a base and retainers that enclose the support column in an annular shape, in several planes. The retainers consist of rings with continuations in the radial direction, wherein sample tubes can be clamped between adjacent continuations. Four such retainers can be provided above one another, such that two sample tubes can be mounted one above the other and are each held at two places.

A disadvantage of this solution is that this retainer cannot be easily loaded or unloaded unless it is taken out of the pneumatic-tube container. It is therefore not particularly suitable for automatic loading and automatic unloading.

It is known from patcit0002:EP 2657160A—.

defining the generic type in question, to provide the pneumatic-tube container with channels into which the sample tubes can be pushed. The channels offer sufficient space for at least two sample tubes arranged one behind the other. To ensure that an individual sample tube cannot slip back and forth in each channel (which may lead to hemolysis), each channel accommodates at least two clamping elements, which protrude laterally into the channel, such that an individual sample tube can also be securely clamped irrespective of its position in the channel.

This solution has the advantage that the sample tubes can be pushed in and removed without the element with the channels having to be withdrawn from the pneumatic-tube container. However, for unloading, it is necessary that the pneumatic-tube container is opened at both sides and that a pusher, having a number of rods corresponding to the number of channels, is driven into the pneumatic-tube container from one side such that the sample tubes can be pushed out at the other side. This is also relatively complicated.

SUMMARY OF THE INVENTION

It is an object of the present invention to make available a pneumatic-tube container which is of the type mentioned at the outset, which can be easily loaded with sample tubes, and from which the sample tubes can be easily removed, with no danger of hemolysis.

According to the invention, this object is achieved by a pneumatic-tube container of the type mentioned at the outset, by virtue of the fact that the clamping element is movable out of the channel, and that this movement out of the channel and into same is coupled to the movement of the cover from the closed position to the open position and from the open position to the closed position, respectively.

In this way, the pneumatic-tube container only has to be opened at one side in order for the clamping elements to be released, and the sample tubes fall out when the opened side of the pneumatic-tube container is held downward. Such a pneumatic-tube container can therefore be automatically emptied just as easily as a pneumatic-tube container in which the sample tubes are transported in an unsecured manner. However, since the sample tubes are clamped during the transport of the pneumatic-tube container, there is no danger of hemolysis occurring.

Two types of covers are in common use on pneumatic-tube containers. In one type, the cover consists of several (three) sectors, which are articulated on an actuation ring and which are movable from the closed position to the open position by displacement of the actuation ring. Such a pneumatic-tube container is known from patcit0003:EP697354A—.

for example. In such a cover, the present invention can be realized by virtue of the fact that the clamping element or the clamping elements are mounted on a cylinder which is mounted in the container cylinder coaxially thereto, that this cylinder is rotatable about its longitudinal axis, and that the cylinder, in order to provide a slotted guide, has an obliquely extending slit into which a pin of the conjointly rotationally guided actuation ring engages such that a displacement of the actuation ring effects a rotation of the cylinder. The clamping element is elastic here and, when the cover is closed, protrudes into the channel, and, when a sample tube is located at this position, the clamping element presses against the sample tube with elastic deformation and securely clamps it. As the tube is rotated when the cover is opened, the clamping element pivots out of the channel and frees the sample tube.

This solution can also be realized if the base also has several base sectors, which are articulated on an actuation ring and which are movable from the closed position to the open position by displacement of the actuation ring, i.e. if the pneumatic-tube container can be opened at both ends in the same way. In this case, provision is made that the cylinder for each actuation ring has an obliquely extending slit into which in each case a pin of the corresponding actuation ring engages, that the two obliquely extending slits are inclined in the same direction, and that each obliquely extending slit, at its end facing the respective end of the container cylinder, merges into a slit which extends in the circumferential direction of the cylinder, such that, by opening of only the cover or of only the base, the clamping element or the clamping elements are moved out of the respective channel in each case in a different direction.

On the other hand, pneumatic-tube containers are also known in which the cover is pivotable about an axis parallel to the longitudinal axis of the container cylinder. Such a pneumatic-tube container is disclosed in patcit0004:EP 2657160 A—.

already mentioned. In such a pneumatic-tube container, the present invention can be realized by virtue of the fact that the clamping element or the clamping elements are mounted on a cylinder which is mounted in the container cylinder coaxially thereto, that this cylinder is rotatable about its longitudinal axis, and that the rotation movement of the cylinder is coupled to the pivoting movement of the cover. This coupling can be achieved quite simply by a corresponding toothing.

BRIEF DESCRIPTION OF THE DRAWINGS

The present invention is explained in greater detail with reference to the attached drawings.

DETAILED DESCRIPTION OF THE INVENTION

The pneumatic-tube container 10 has, as is customary, a container cylinder 11, a cover 12 and a base 13; a slide ring 14 is mounted on the cover 12, and a slide ring 15 is mounted on the base 13. When the pneumatic-tube container 10 is located in a forwarding tube of the pneumatic-tube system, the slide rings 14, 15 bear tightly on the forwarding tube such that the pneumatic-tube container 10 is guided in the forwarding tube and can be transported by a pressure difference in the forwarding tube.

The cover 12 is composed of three cover sectors 12a to 12c. Accordingly, the slide ring 14 also consists of three parts 14a to 14c, wherein each cover sector 12a to 12c carries a corresponding part 14a to 14c of the slide ring 14. Each of the cover sectors 12a to 12c is mounted pivotably on an actuation ring 17 by means of a rotation axle, with only the rotation axles 16a and 16b of the cover sectors 12a and 12b being visible in the figures. The actuation ring 17 is arranged around the container cylinder 11 and is displaceable in the direction of the longitudinal axis 19 of the container. Therefore, the rotation axles 16a, 16b of the three cover sectors 12a, 12b, 12c are also located just outside the container cylinder 11. They also extend perpendicularly with respect to the longitudinal axis 19 of the container and tangentially to the container cylinder 11. The cover sectors 12a to 12c can therefore be pivoted about the rotation axles 16a, 16b to an open position, and, by a displacement of the actuation ring 17, they are able to slide past the container cylinder 11 (see FIGS. 4 to 7).

The actuation ring 17 has a projection 17a, such that pneumatic-tube containers 10 of this type can easily be automatically opened: A gripper of the pneumatic-tube station comes to bear on the projection 17a, and the slide ring 17 is displaced and the container opened only when the gripper is moved and the pneumatic-tube container 10 is held secure or when the pneumatic-tube container 10 is moved relative to the stationary gripper.

Pneumatic-tube containers 10 of this kind can also be designed to be self-closing in a simple way, by means of the cover sectors 12a to 12c being spring loaded in the direction of the closed position.

To allow sample tubes 20 to be transported using a pneumatic-tube container 10 of this kind, an insert 21 is inserted into the container cylinder 11. This insert 21 has groove-like depressions 22 which, together with the container cylinder 11, form channels 23 into which the sample tubes 20 can be pushed. In the exemplary embodiment, there are ten such channels 23, which can each receive three short sample tubes 20, such that up to a total of thirty sample tubes can be transported. In an alternative to this, each channel 23 can receive two long sample tubes.

Figure 1:
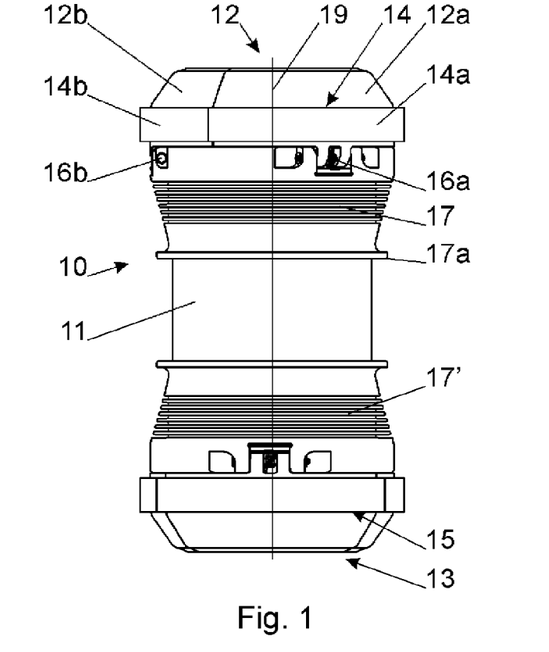
FIG. 1 shows a side view of a first embodiment of a pneumatic-tube container according to the invention in a closed position.
Figure 2:
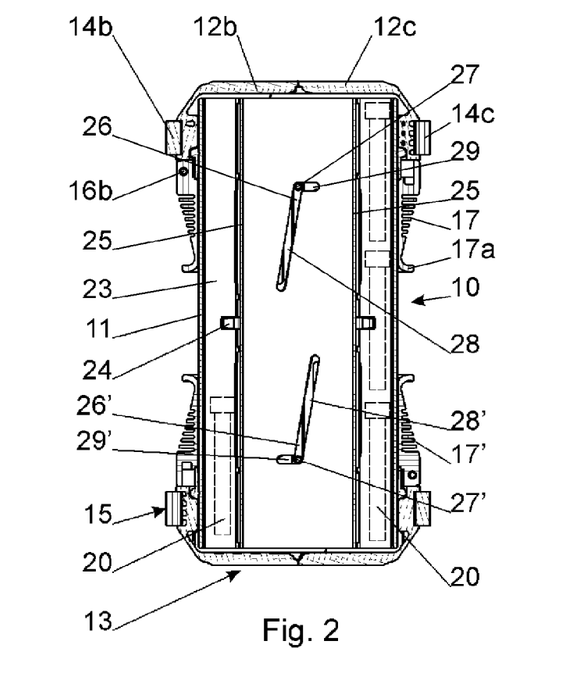
FIG. 2 shows the same in longitudinal section.

As long as three short or two long sample tubes are inserted in each channel 23, their movement clearance is slight. However if only one sample tube 20 is inserted (shown on the left in FIGS. 2 and 5), the following problem arises: If the pneumatic-tube container 10 is transported upward and is then braked, the sample tube 20 initially moves farther on in the same direction, i.e. upward in relation to the pneumatic-tube container 10, until it strikes the cover 12. However, along this distance of about 15-20 cm, the pneumatic-tube container 10 was already braked quite considerably, with the result that the speed difference between sample tube 20 and cover 12 is quite considerable upon impact. Directly after the impact, the sample tube 20 then falls back downward and makes renewed impact. In this way, hemolysis can arise under unfavorable circumstances, as a result of which the blood sample becomes unusable. If the pneumatic-tube container 10 is transported downward, a similar problem arises on acceleration.

To prevent hemolysis, a clamping element 24 made of elastic material is now provided in each channel 23. If three sample tubes 20 are inserted (on the right in FIGS. 2 and 5), this clamping element 24 presses against the middle sample tube with corresponding deformation. If only one sample tube is inserted (on the left in FIGS. 2 and 5), the clamping element 24 then protrudes into the channel, such that the sample tube 20 can only move a few centimeters and moreover, on account of the elasticity of the material of the clamping element 24, makes a relatively gentle impact.

Figure 3:
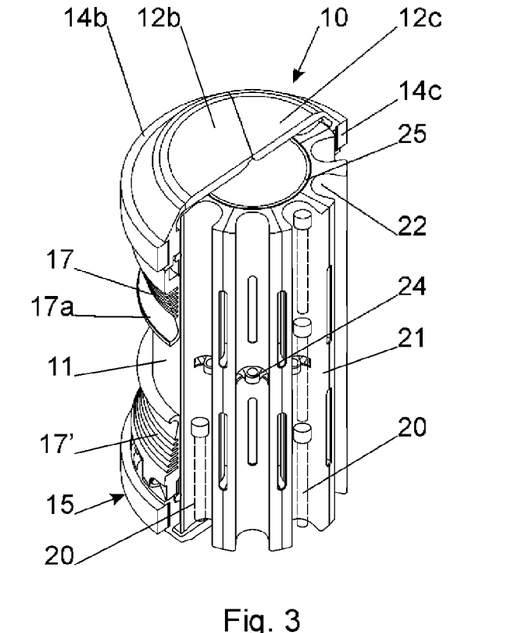
FIG. 3 shows the same in a perspective view, in which the container cylinder and the two container heads are half broken away.
Figure 4:
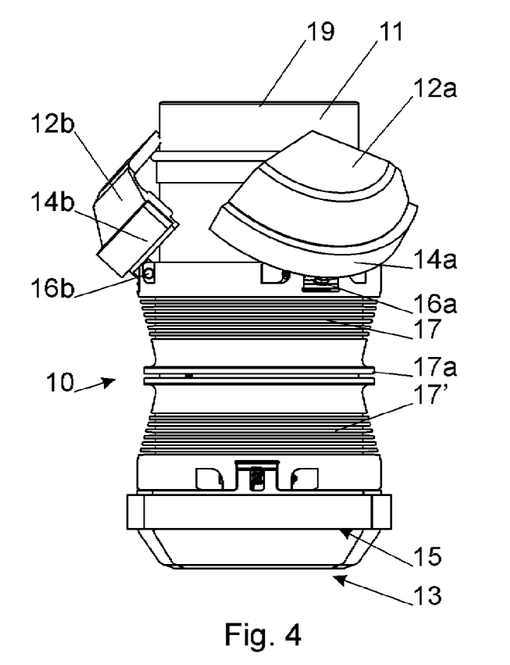
FIGS. 4 to 6 show this pneumatic-tube container in views corresponding to those of FIGS. 1 to 3, but in the open position.
Figure 5:
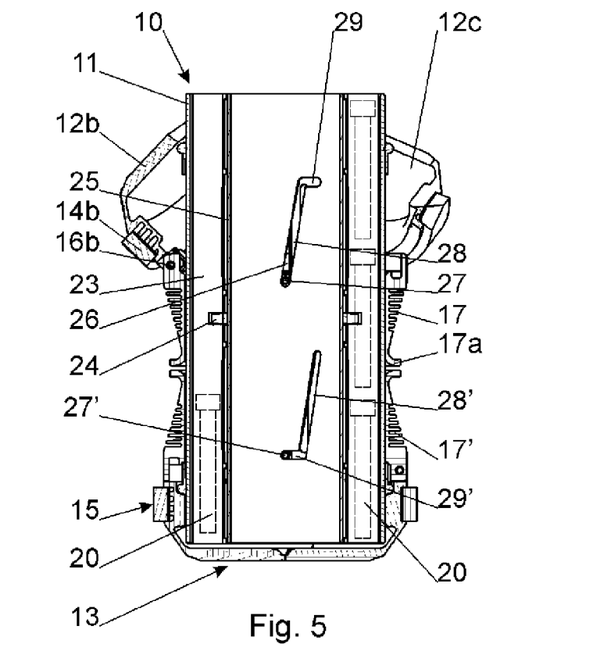
Figure 6:
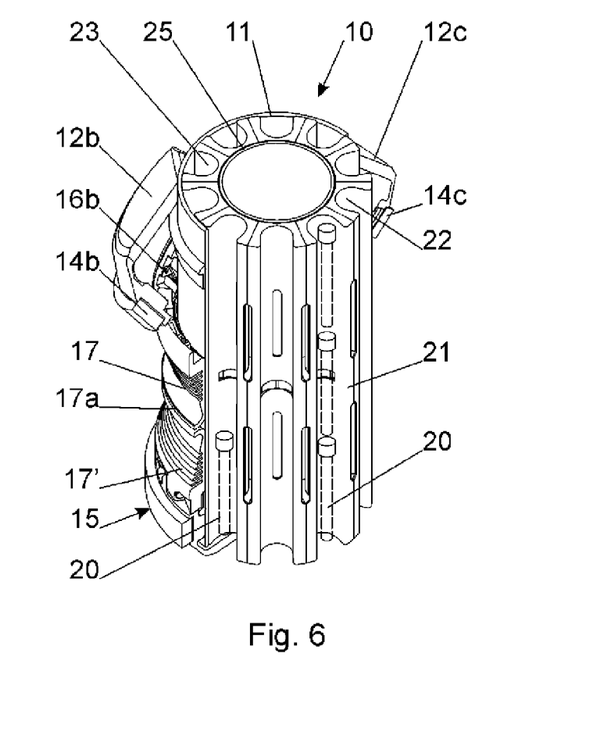
Figure 7:
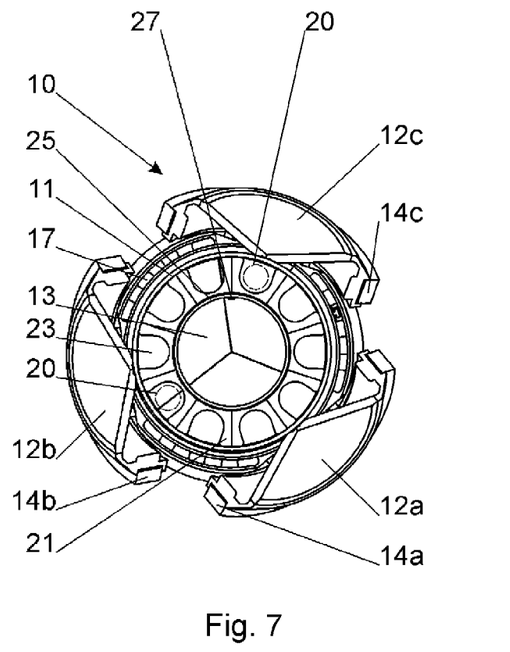
FIG. 7 shows this pneumatic-tube container in the open position from above.
Figure 8:
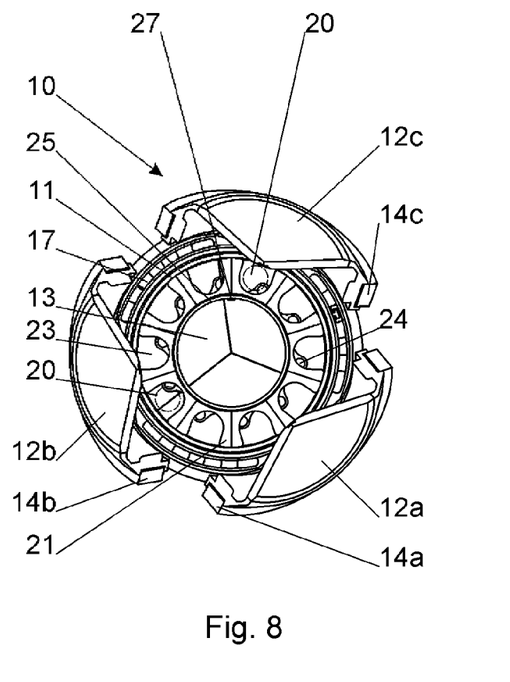
FIG. 8 shows this pneumatic-tube container in a half-opened position from above.

However, as a result of the clamping elements 24, it is not now possible for all of the sample tubes 20 to fall out of the pneumatic-tube container 10 if the latter is held with the opening facing downward. For this reason, provision is made according to the invention that the clamping elements 24 are mounted on a cylinder 25 which is coaxial to the container cylinder 11 and rotatable with respect to this container cylinder 11, but axially undisplaceable. If the cylinder 25 is rotated, the clamping elements 24 pivot laterally out of the groove 22 (compare FIG. 3 with FIG. 6, and FIG. 7 with FIG. 8). As soon as the clamping elements 24 are pivoted out of the respective grooves 22, all of the sample tubes 20 fall out of the pneumatic-tube container simply under the effect of gravitational force.

To ensure that this rotation of the cylinder 25 takes place automatically when the pneumatic-tube container 10 is opened, an axially parallel slit 26 is provided in the container cylinder 11 (only seen in FIGS. 2 and 5, and there only partially, behind the slit 28 explained below), and a pin 27 inserted into the actuation ring 17 engages through the slit 26. During the opening and closing of the pneumatic-tube container 10, the pin 27 slides downward and upward in this slit 26. In the cylinder 25, there is an obliquely extending slit 28 in which the pin 27 likewise engages. In this way, a slotted guide is obtained which, upon opening and closing of the pneumatic-tube container 10, effects a corresponding rotation of the cylinder 25. In other words, when the pneumatic-tube container 10 is opened, the clamping elements 24 are pivoted out of the channels 23 and, when the pneumatic-tube container 10 is closed, they are pivoted into the channels 23.

It is of course necessary that the insert 21 has a slit (or at this point an opening) which is flush with the slit 26 in the container cylinder 11, such that the movement of the pin 27 is not impeded by the insert 21.

Pneumatic-tube containers 10 are often symmetrical in shape, i.e. the base 13 is designed like the cover 12. Therefore, the base 13 also consists of three segments which are mounted on an actuation ring 17'. To allow the clamping elements 24 to pivot out during opening of the base 13, a further slit 26' (only seen in FIG. 2 and there also just partially, behind the slit 28' just explained) is provided in the container cylinder 11, and a pin 27' of the actuation ring 17' of the base 13 engages through the slit 26'. This pin 27' engages in a further, obliquely extending slit 28' of the cylinder 25, such that the latter rotates as the base 13 is opened. To ensure that the slotted guide of the cover 12 does not block this movement, the obliquely extending slit 26 merges at its upper end into a horizontal slit 29 (i.e. a slit extending in the circumferential direction). Analogously to this, the obliquely extending slit 28' merges into a horizontal slit 29', such that the base 13 does not block the opening movement of the cover 12.

Figure 9:
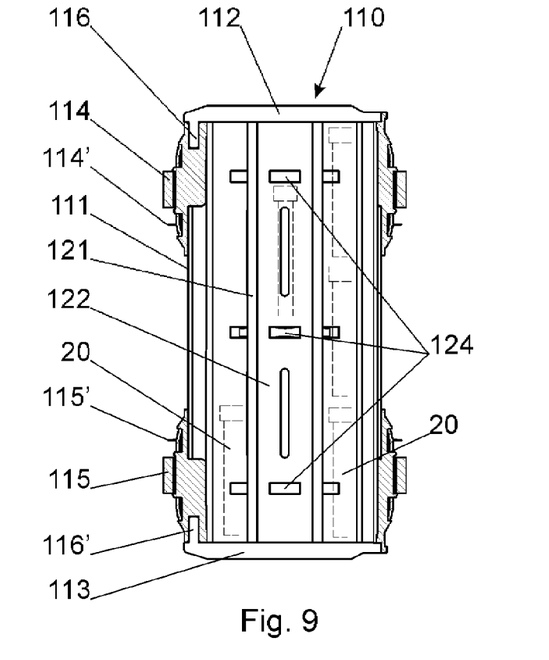
FIG. 9 shows a second embodiment of a pneumatic-tube container in a closed position, in a sectional view along the line IX-IX in FIG. 11.
Figure 10:
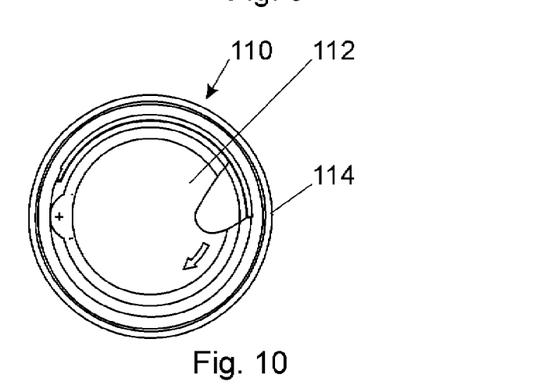
FIG. 10 shows the same from above.
Figure 11:
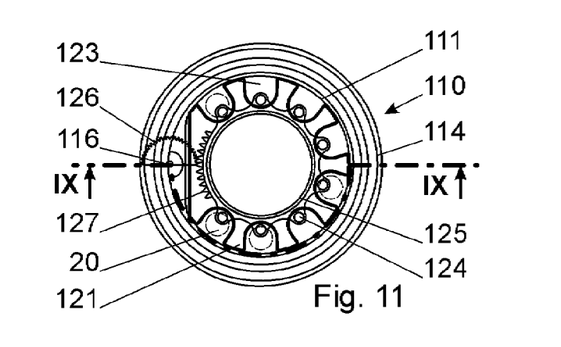
FIG. 11 shows the same from above, but with the cover removed.
Figure 12:
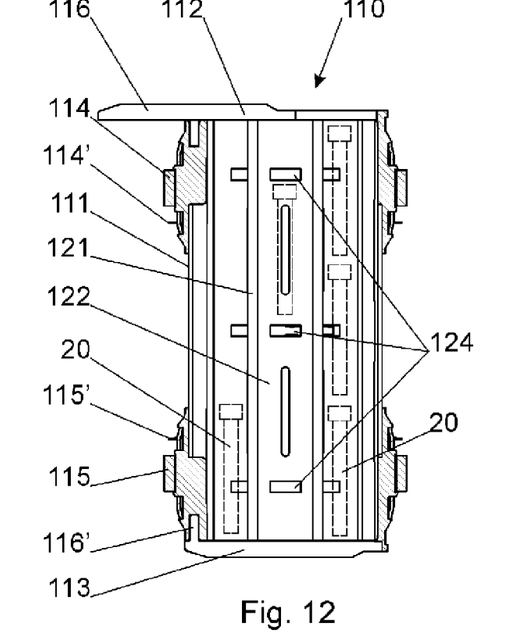
FIGS. 12 to 14 show the same cylinder in views corresponding to those of FIGS. 8 to 10, but in a half-opened position.
Figures 13, 14:
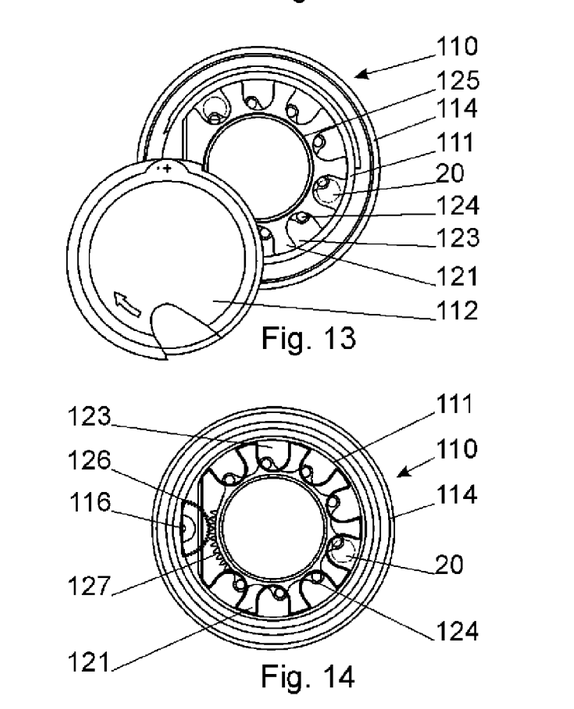
Figure 15:
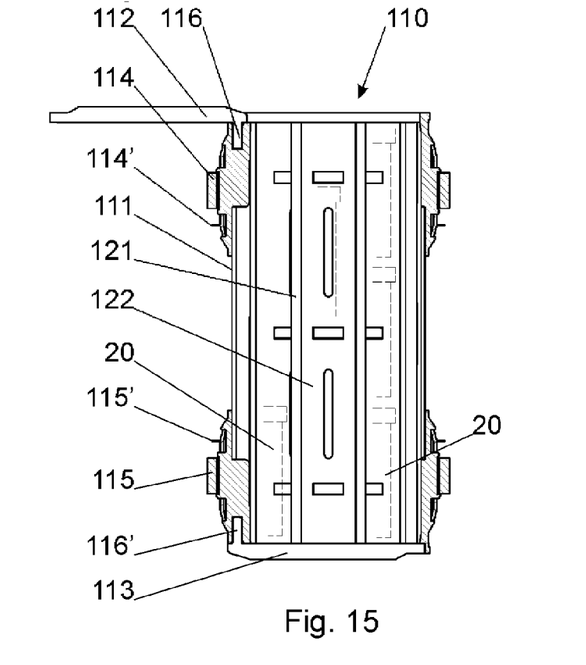
FIGS. 15 to 17 show the same cylinder in views corresponding to those of FIGS. 8 to 10, but in a fully opened position.
Figure 16:
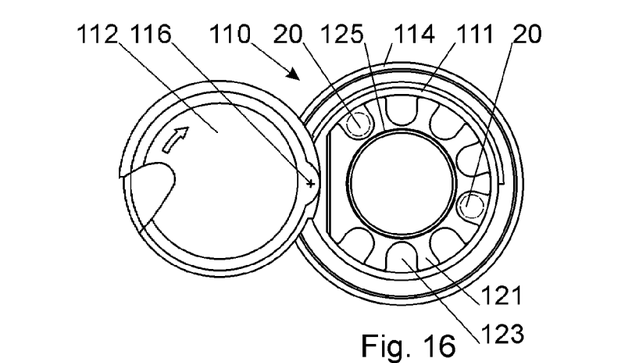
Figure 17:
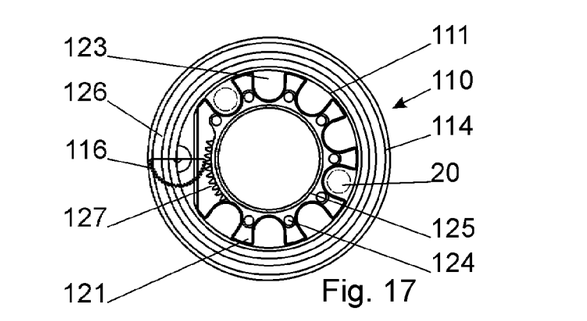

FIGS. 9 to 17 show a pneumatic-tube container 110 with a container cylinder 11, the latter having a cover 112 which is pivotable away from an axle 116 located at the edge of the pneumatic-tube container (cf. FIGS. 9, 12 and 15; 10, 13 and 16; and 11, 14 and 17). Analogously to this, a base 113 is pivotable away from an axle 116'. Independently of cover 112 and base 113, slide rings 114 and 115 are provided on the container cylinder 111, and the sealing in relation to the container cylinder is here effected by sealing rings 114' and 115'.

As in the first embodiment, an insert 121 is provided in the container cylinder 111, wherein the grooves 122 of the insert 121 form channels 123 together with the container cylinder 111, into which sample tubes 20 can be pushed. Similarly, a container 125 is provided which here, however, has for each channel 123 three clamping elements 124 at different heights. Thus, individual short sample tubes are also clamped (left-hand channel in FIG. 9). The cylinder 125 is again mounted so as to be rotatable. The drive is effected via a toothed wheel 126, which meshes in a corresponding toothed ring 127 of the cylinder 125.

If, as is shown, the container cylinder is symmetrical, a corresponding toothed wheel then has to be provided for the base 113, which toothed wheel meshes in a further toothing (not shown) of the cylinder 125. To ensure that the two toothed wheels do not block each other, they must have a gap at the appropriate place in the toothing when the cover 112 is closed and/or when the base 113 is closed. As is shown, they can also be configured as half toothed wheels. To ensure that the cylinder 125 does not rotate unintentionally when both base 113 and also cover 112 are closed and both toothed wheels are thus disengaged, the cylinder 125 should lock in this position, i.e. in the clamping position.

The invention claimed is:

1. A pneumatic-tube container having a container cylinder and having a cover and a base at the two ends of the container cylinder, wherein at least the cover is movable from a dosed position to an open position, wherein the container cylinder accommodates an insert which, in order to receive sample tubes, has at least one tubular channel extending parallel to the longitudinal axis of the container cylinder, wherein at least one channel accommodates at least one damping element, which protrudes laterally into the channel, wherein the clamping element is movable out of the channel, and in that this movement out of the channel and into same is coupled to the movement of the cover from the closed position to the open position and from the open position to the closed position, respectively.

2. The pneumatic-tube container according to claim 1, wherein the cover has several cover sectors, which are articulated on an actuation ring and which are movable from the closed position to the open position by displacement of the actuation ring, wherein the clamping element or the damping elements are mounted on a cylinder which is mounted in the container cylinder coaxially thereto, wherein the cylinder is rotatable about its longitudinal axis, and the cylinder, in order to provide a slotted guide, has an obliquely extending slit into which a pin of the conjointly rotationally guided actuation ring engages, such that a displacement of the actuation ring effects a rotation of the cylinder.

3. The pneumatic-tube container according to claim 2, wherein the base also has several base sectors, which are articulated on an actuation ring and which are movable from the dosed position to the open position by displacement of the actuation ring, wherein the cylinder has for each actuation ring an obliquely extending slit into which in each case a pin of the corresponding actuation ring engages, wherein the two obliquely extending slits are inclined in the same direction, and each obliquely extending slit, at its end facing the respective end of the container cylinder, merges into a slit which extends in the circumferential direction of the cylinder, so that, by opening only of the cover or only of the base, the clamping element or the clamping elements are moved out of the respective channel in each case in a different direction.

4. The pneumatic-tube container according to claim 2, wherein the cover is pivotable about an axis parallel to the longitudinal axis of the container cylinder, wherein the damping element or the clamping elements are mounted on a cylinder which is mounted in the container cylinder coaxially thereto, in that this cylinder is rotatable about its longitudinal axis, wherein the rotation movement of the cylinder is coupled to the pivoting movement of the cover.

\* \* \* \* \*